United States Patent
Amner et al.

[11] Patent Number: 5,786,892
[45] Date of Patent: Jul. 28, 1998

[54] PLASTICS IDENTIFICATION

[75] Inventors: John Amner, Rochford; Steve Miles, Kelvedon Hatch; Peter Mucci, Southampton, all of Great Britain

[73] Assignee: Ford Global Technologies, Inc., Dearborn, Mich.

[21] Appl. No.: 732,483
[22] PCT Filed: Apr. 5, 1995
[86] PCT No.: PCT/GB95/00779
 § 371 Date: Sep. 30, 1996
 § 102(e) Date: Sep. 30, 1996
[87] PCT Pub. No.: WO95/27892
 PCT Pub. Date: Oct. 19, 1995

[30] Foreign Application Priority Data

Apr. 7, 1994 [GB] United Kingdom ............ 9406842
Aug. 10, 1994 [GB] United Kingdom ............ 9416159

[51] Int. Cl.$^6$ ............................................. G01N 21/01
[52] U.S. Cl. .................................... 356/244; 356/36
[58] Field of Search ................................. 356/244, 246, 356/36, 440, 300, 319, 326; 15/304; 250/576

[56] References Cited

U.S. PATENT DOCUMENTS 4,644,163 2/1987 Selander ............................... 356/371
5,281,798 1/1994 Hemm et al. ........................ 250/226

*Primary Examiner*—Hoa Q. Pham
*Attorney, Agent, or Firm*—Damian Porcari

[57] ABSTRACT

To enable a spectrometer (10) to be used for taking analysis readings from plastics articles (24) of varying shapes and degree of preparation, the spectrometer (10) is enclosed within a housing which has an interface device (14) attached to the sensing window (58). The interface device (14) is sensitive to the positioning of a sample (24) in position to carry out sample preparation tasks as the sample is brought into the analysis position opposite the sensing window (58). The interface device (14) comprises a front wall (16) with a sample aperture (18) against which the sample (24) can be placed so that a surface of the sample (24) is exposed through the aperture (18), means (48) for cleaning a sample surface (24) placed against the front wall (16), means (52) for extracting debris resulting from the sample cleaning, and means (30, 32) for guiding the front wall (16) towards the sensing window (58) to enable the spectrometer (10) to take a reading from the sample surface (24).

16 Claims, 4 Drawing Sheets

ём
5,786,892

PLASTICS IDENTIFICATION

BACKGROUND OF THE INVENTION

1. Field of the Invention

This invention relates to an apparatus for identifying different plastics materials. The apparatus is particularly (but not exclusively) suitable for use in the plastics industry, for separating plastics components into chemically similar groups as a first stage in, for instance, the recycling of the plastics materials.

2. Description of the Related Arts

One field of application is the recycling of motor car components. When a motor car is scrapped, its saleable components such as battery, tires or radio are removed, usually for use in other vehicles. The metal parts of the scrap car are generally re-cycled, and what remains is shredded and used as land-fill.

The remainder that is used for land-fill consists primarily of a mixture of plastics materials. For environmental and/or economic reasons, it is desirable to be able to recycle such waste plastics materials. However it is not possible effectively to recycle mixtures of waste plastics without first separating the plastics into chemically similar groups or families. Failure to achieve this separation would mean that unknown portions of different plastics were incorporated in the melt during the reclaim process. The presence of other plastics components in a blend may necessitate changes in processing conditions or lead to unacceptable changes in the physical properties of the finished recycled material.

Whilst a number of laboratory techniques are known for identifying different plastics materials, none of these are suitable for use in a continuously operating plastics recycling line, and none of them can cope easily with scrap motor car parts which are of irregular size and shape and are usually dirty.

European patent publication number 0 497 397 discloses apparatus for identifying plastics materials, the apparatus comprising a light source for producing short wave light impulses, spectral apparatus for producing an emission spectrum, a detector for converting the radiation intensities into electrical signals, and a computer for processing the electrical signals to produce sorting signals. The apparatus is used with particles of plastics materials which are carried by a conveyor belt from a delivery station. When a particle of plastics material passes a pre-set point by the apparatus it breaks a light beam, triggering the light source to take a reading. The reflection spectrum from a plastics material is used to identify that material and allow like materials to be sorted together. The surface of a particle of plastics material may be partially cleaned by means of a laser beam to remove surface dirt.

Our co-pending International Patent Application number PCT GB93/02244 describes a method and an instrument for identifying plastics materials using a spectroscopy technique.

While spectroscopy can lead to accurate results in terms of plastics identification, the instrumentation required is delicate and has to be carefully set up and maintained.

The present invention therefore seeks to provide an interface between spectroscopy apparatus and a piece of plastics to be identified, which will allow plastics components of a wide variety of shapes and conditions to be brought into a uniform position where they can be tested by the apparatus.

SUMMARY OF THE INVENTION

According to the present invention, there is provided apparatus for identifying plastics, the apparatus comprising a spectrometer, characterised in that the apparatus further comprises a protective casing surrounding the spectrometer with a sensing window formed in one face of the casing, and an interface device associated with the sensing window, the interface device comprising a front wall with a sample aperture against which the sample can be placed so that a surface of the sample is exposed through the aperture, means for cleaning a sample surface placed against the front wall, means for extracting debris resulting from the sample cleaning, and means for guiding the front wall towards the sensing window to enable the spectrometer to take a reading from the sample surface.

It is a feature of the invention that the sample is positioned once on the front wall, and thereafter only needs to be held in contact with the front wall and pushed forward with the front wall until the reading has been taken.

The guiding means preferably comprises a set of tracks along which the front wall can move linearly towards the sensing window, with the front wall being urged to the end of the tracks remote from the window.

The chamber is preferably surrounded and possibly enclosed by side walls in the form of collapsible bellows. The front wall may be displaceable towards and away from the sensing window of the spectrometer casing, and the displacement may be accomplished by mounting the front wall on spring-loaded guide rods which allow the front wall to be moved towards the sensing window, up to a defined end position at which a spectrometer reading will be taken.

The sample surface cleaning means, the debris extraction means and the purging medium feed means, when present, may all be sequentially operated by switches which are tripped in turn as the front wall is displaced towards the sensing window of the spectrometer casing. The mechanisms for sample surface cleaning, for debris extraction and for introduction of purging medium may all be constructed in such a way that they are brought into position between the front wall and the sensing window, when they are operated, and are automatically moved out of the region between the front wall and the sensing window when their function has been completed.

The sample surface cleaning means may be a grinding wheel, router or similar device which rotates in contact with the sample surface through the sample aperture of the front wall.

The debris extraction means can be a suction pipe which uses suction to extract debris, particularly debris produced by the action of the sample surface cleaning. The debris extraction means may operate simultaneously with the sample surface cleaning means.

In a preferred embodiment the sample surface cleaning means is contained within a housing inside the interface device chamber. The housing may be provided with means for sweeping away and collecting swarf which is produced by the cleaning of the sample surface. The housing may be provided with a tube or other conduit through which the swarf passes to be collected by collection means. A partial vacuum may be applied via the tube to help with the removal of swarf from within the housing by suction. This embodiment permits more efficient collection and removal of swarf.

The purging medium feed means will preferably fill the chamber with an inert medium at a positive pressure, prior to the spectrometer reading being taken. The use of a positive pressure will prevent ingress of particles into the chamber.

3

BRIEF DESCRIPTION OF THE DRAWINGS

The invention will now be further described, by way of example, with reference to the accompanying drawings, in which.

DETAILED DESCRIPTION OF THE PREFERRED EMBODIMENTS

Figure 1:
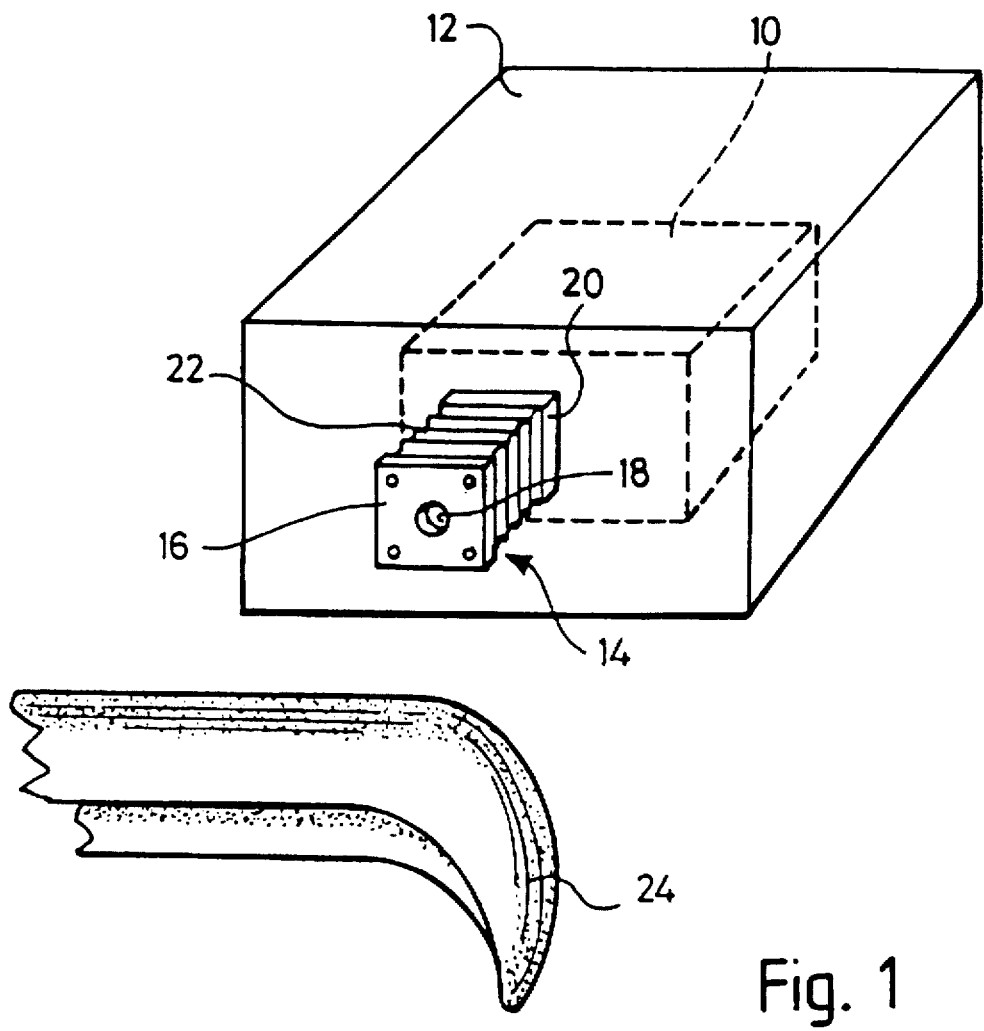
FIG. 1 is a schematic view of a plastics identification apparatus according to the invention, and also showing a plastics item to be identified.
Figure 1A:
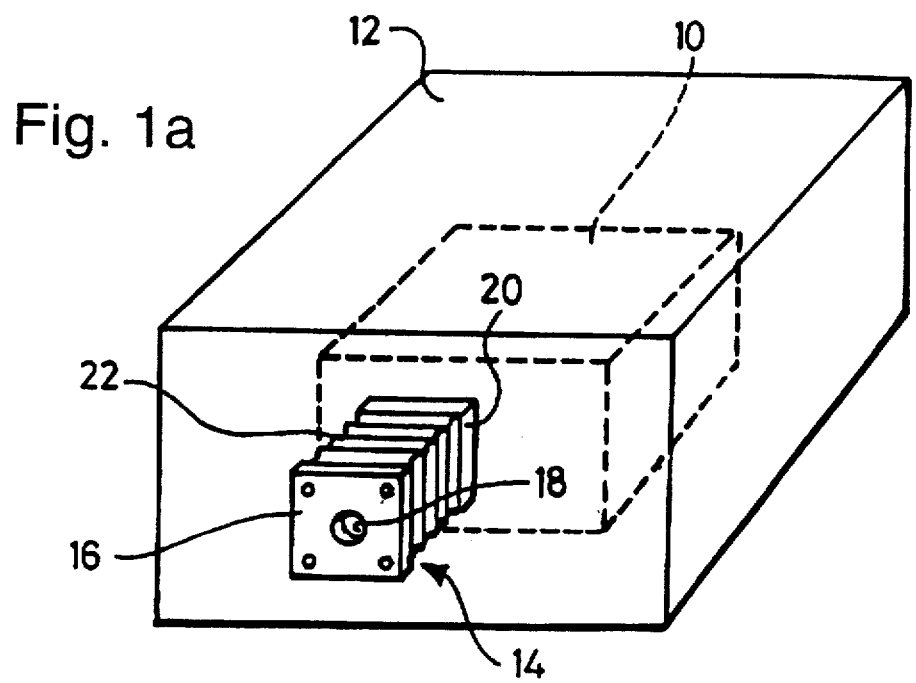
Figure 1B:
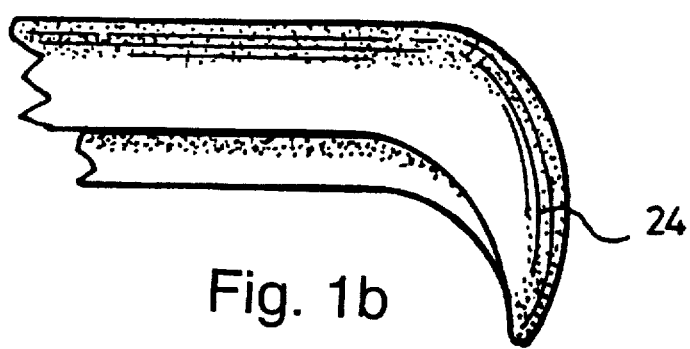

FIG. 1 shows a spectrometer 10 indicated in dotted lines which is housed within a protective housing 12. The protective housing protects the delicate spectrometer instrument from dirt and other foreign matter and from physical shocks. The housing is therefore continuous around the spectrometer instrument, apart from a sensing aperture or window 58 through which the spectrometer can look at a sample to be analysed.

On one face of the casing 12 there is a sample interface device 14. This device consists of a front wall 16 with a sample aperture 18, a back wall 20 mounted on the outer surface of the housing 12 and a flexible bellows 22 which encloses a chamber between the front wall 16 and the back wall 20. The back wall has an opening 57 which is closed by a shutter 56, and which registers with the sensing window 58 of the housing 12.

A sample to be identified, in this case a motor vehicle bumper 24, is placed against the sample window 18, as will now be described with reference to FIG. 2.

Figure 2:
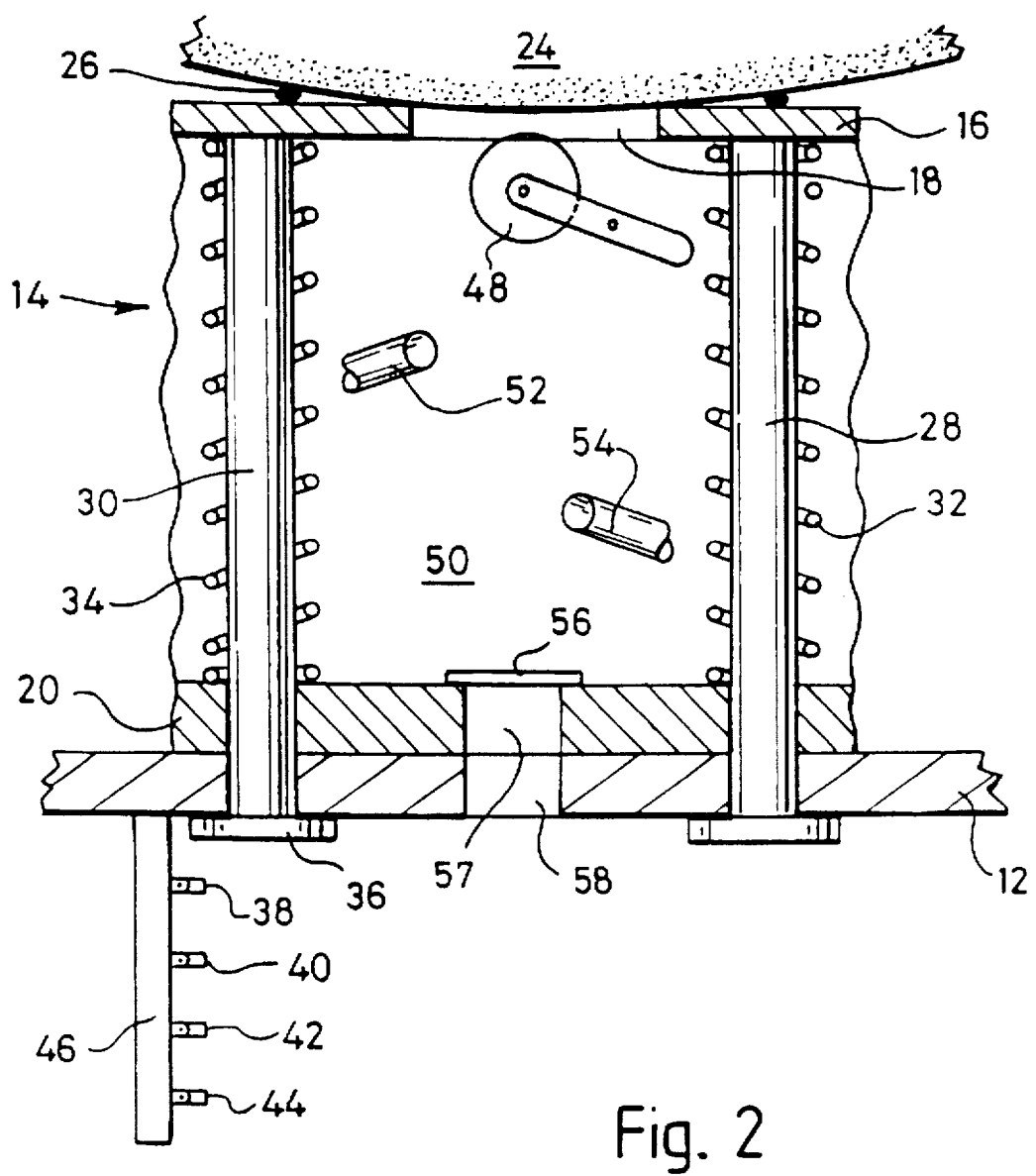
FIG. 2 is a cross-section through part of the apparatus of FIG. 1.

In FIG. 2 the vehicle bumper 24 (which has a curved rather than a flat surface) is placed against the front wall 16 so that it covers the sample aperture 18. It may be desirable to place a compressible rubber seal 26 around the aperture 18 so that part of the bumper 24 within the seal is sealed against the outside environment.

To take a reading, the operator holds the bumper 24 against the front wall 16 and exerts pressure on the bumper which gradually pushes the bumper and the front wall towards the protective housing 12. The front wall is mounted on guide rods 28, 30 which are biased away from the housing 12 by compression springs 32, 34. The force of these springs can however be overcome by the pressure which the operator exerts on the bumper.

As the inner ends of the guide rods 28, 30 pass into the interior of the casing 12, a foot 36 on the rod 30 moves past switch levers 38, 40, 42, 44 on a switch mounting arm 46. After the first stage of inward movement, the switch lever 38 is tripped and this triggers operation of a grinding wheel 48 which rotates to grind a clean surface area on the bumper. The purpose of this grinding step is to remove any surface treatments such as paint and/or surface grime which may have accumulated on the surface.

As the movement of the front wall 16 towards the housing continues, the foot 36 will next operate the switch lever 40 which will stop operation of the surface cleaning, will cause the grinding wheel to be moved away from the sample aperture, and will start a debris extraction routine which

4 extracts any debris contained within the chamber 50 through a suction pipe 52.

When the foot 36 reaches the third switch lever 42, debris extraction will stop, the pipe 52 will be moved away from the sample aperture, and the chamber 50 will be purged by introducing an inert gas through a gas pipe 54.

Finally when the foot 36 reaches the last switch lever 44, purging will stop, the pipe 54 will be withdrawn, a shutter 56 which closes a sensing window 58 will be opened, and the spectrometer itself will be activated to take a reading of the clean bumper surface 24.

Once the reading has been taken, a signal is given to the operator, possibly by the illumination of a green light somewhere on the casing, that the bumper can be removed and the springs 32, 34 will then restore the front wall 16 to its original position and the apparatus will be ready for another sample to be put in place and another reading to be taken.

Figure 3:
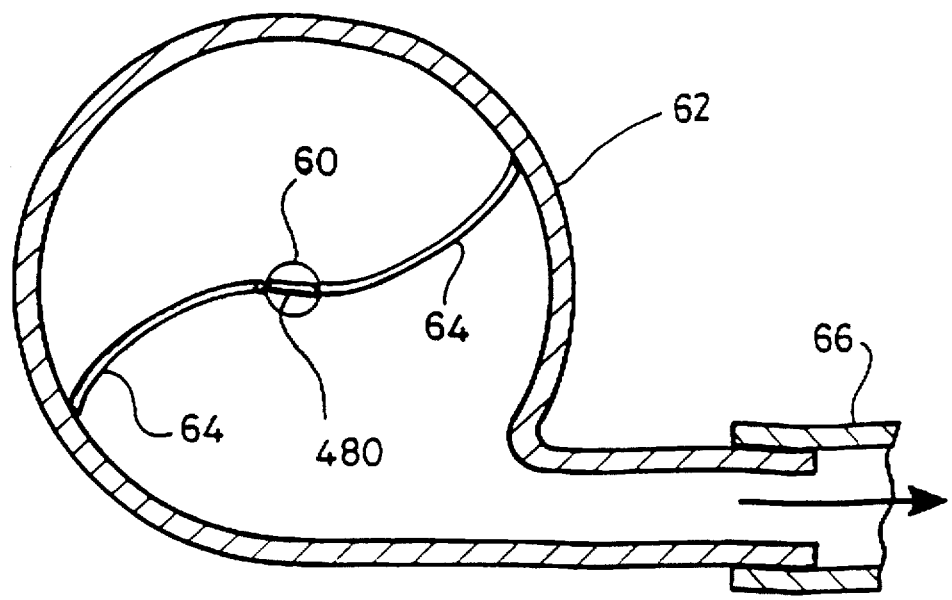
FIG. 3 is a cross-section through a part of a preferred grinder housing arrangement for use with the apparatus of FIG. 1.

FIG. 3 shows a preferred assembly for cutting a clean surface on a sample. A rotatable cutting blade 480 is mounted on a spindle 60, and the spindle is provided with two sweeping members 64. The assembly is contained within a housing 62 which is connected to a tube 66 for conveying swarf to a swarf bin. In operation the blade 480 cuts or mills the sample surface, and the sweeping members 64 act to sweep swarf from the sample surface down the tube 66 to a bin (not shown). Suction may be applied to the tube 66 to aid in swarf removal, and the assembly may be used in addition to, or instead of, the debris extraction routine described above.

Figure 4:
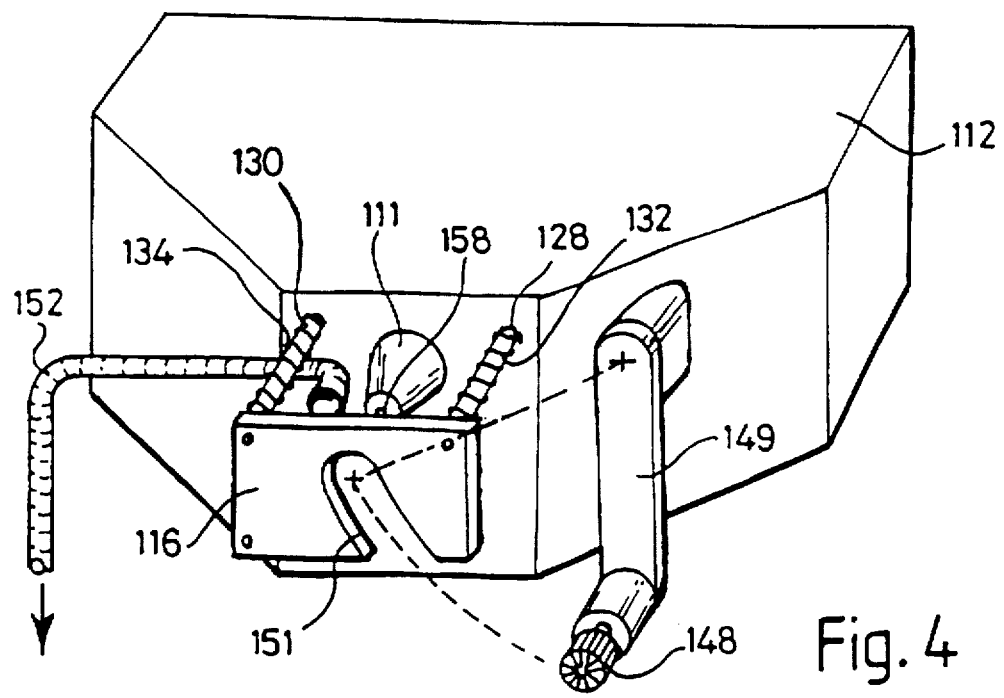
FIG. 4 is a view corresponding to FIG. 1 but showing a second embodiment of the invention.

FIG. 4 shows an alternative embodiment where the space between the front wall 116 and the spectrometer casing 112 is not enclosed.

The spectrometer casing has a turret 111 and the sensing window 158 is at the tip of this turret. In this embodiment, no steps are taken to purge the atmosphere surrounding the turret, but a pipe 152 is used to extract dust and swarf from the prepared sample surface. This pipe 152 can be housed, in part, in the space surrounding the turret 111.

The front wall 116 is mounted on posts 128, 130 surrounded by coil springs 132, 134. There are three of these posts. The fourth corner of the front wall is not supported by a post but is designed to allow access to a milling cutter 148 which is mounted on a swing arm 149. The front wall 116 has an arcuate track 151 to allow entry of the cutter 148 to a position where it cuts the sample surface directly in the position where the sample will register with the sensing window 158. The cutter will be set slightly proud of the front wall 116 and will cut a track through the sample surface as it swings in. The rotation of the cutter and the movement of the swing arm can both be started by a contact switch which is triggered when a sample is placed against the front wall 116.

The cutter could alternatively move along a linear path to the centre of the front wall 116.

The space between the front wall 116 and the spectrometer housing could be shielded on two or three sides to restrict dust entry and to improve appearance.

A shutter over the sensing window 158 will be opened automatically when the front wall 116 is pushed up against the turret 111, to enable the spectrometer to take a reading from the prepared sample surface.

Although a spectrometer can produce very accurate results in respect of plastics identification, a spectrometer instrument is a delicate instrument, the setting and handling of which requires considerable skill. Using an interface as described here between the spectrometer and the sample to be identified allows the spectrometer to be isolated from the environment and yet to be used for taking quick readings of a number of different samples.

We claim:

1. An apparatus for identifying different plastic materials comprising;

a spectrometer (10), a protective casing (12, 112), surrounding the spectrometer (10) and defining a sensing window (58, 158) formed in one face of the casing (12, 112);

an interface device (14) associated with the sensing window (58, 158), of the interface device (14) having a front wall (16, 116) defining a sample aperture (18, 118) against which a sample (24) can be placed so that a surface of the sample (24) is exposed through the aperture (18, 118);

means (48, 148, 480) for cleaning a sample surface (24) placed against the front wall (16, 116);

means (52, 152) for extracting debris resulting from the sample cleaning; and means (28, 30, 128, 130) for guiding the front wall (16, 116) towards the sensing window (58, 158) to enable the spectrometer (10) to take a reading from the sample surface (24).

2. The apparatus as described in claim 1, wherein the guiding means (28, 30, 128, 130) comprises a set of tracks along which the front wall (16, 116) can move linearly towards the sensing window (58, 158), and the guiding means being provided with means (32, 34, 132, 134) for urging the front wall (16, 116) to the end of the tracks remote from the window (58, 158).

3. The apparatus as described in claim 2, wherein the tracks are posts (128, 130) surrounded by coil springs (132, 134), with the springs (132, 134) normally urging the front wall (116) away from the sensing window (158), and being compressed when the front wall (116) is moved towards the window (158).

4. The apparatus as described in claim 3, wherein a chamber (50) is enclosed by the front (16), a back wall (20) and by side walls, the side walls include a collapsible bellows (22).

5. The apparatus as described in claim 4, further comprising means (52, 152) for extracting debris resulting from the sample surface cleaning is provided between the front wall (16, 116) and the sensing window (58, 158).

6. The apparatus of claim 5, wherein the debris extraction means is a suction pipe (152) which uses suction to extract debris, particularly debris produced by the action of the sample surface cleaning.

7. The apparatus is claimed in claim 5, wherein the debris extraction means (152) is adapted to operate simultaneously with the sample surface cleaning means (480).

8. The apparatus as described in claim 4, further comprising means (54) for feeding a purging medium into the enclosed chamber (50).

9. The apparatus as described in claim 8, further comprising a turret (111) extending from the spectrometer casing (112) having the sensing window (158) at the end of the turret. (111).

10. The apparatus of claim 8 further comprising a switch (38) which is tripped as the front wall (16, 116) is dispensed towards the sensing window (58, 158) of the spectrometer casing (12, 112) and operates the sample surface cleaning means (48, 148, 480).

11. The apparatus is described in claim 10 further comprising switches (38, 40, 42) which are tripped as the front wall (16) is dispensed towards the sensing window (58) of the spectrometer casing (12) and engage a sample surface cleaning means (48, 480), the debris extraction means (52) and the purging medium feed means (54).

12. The apparatus as described in claim 11, wherein the mechanisms for sample surface cleaning (48, 480), for debris extraction (50) and for introduction of purging medium (52) are all moveable between the front wall (16) and the sensing window (58).

13. The apparatus of claim 8, wherein the purging medium feed (54) means is adapted to fill the chamber (50) with an inert medium at a positive pressure, prior to the spectrometer reading being taken.

14. The apparatus of claim 1, wherein the sample surface cleaning means comprises a rotary cutter (480).

15. The apparatus of claim 1, wherein the sample surface cleaning means is a grinding wheel (48) which rotates in contact with the sample surface through the sample aperture (18) of the front wall (16).

16. The apparatus of claim 1, wherein the sample surface cleaning means (480) is mounted in a housing (62) which is connected by means of a conduit (66) to a debris collection bin and wherein the surface cleaning means (480) is provided with sweeping means (64) for sweeping debris into the conduit (66).

* * * * *